United States Patent [19]

Matsumoto et al.

[11] Patent Number: 4,917,820

[45] Date of Patent: Apr. 17, 1990

[54] ETHYLENE REMOVAL AGENT, POSTHARVEST PRESERVATION AGENT AND DEODORANT

[75] Inventors: Mutsumi Matsumoto; Masanobu Ogawa, both of Gunma, Japan

[73] Assignee: Nippon Kayaku Kabushiki Kaisha, Tokyo, Japan

[21] Appl. No.: 317,140

[22] Filed: Mar. 1, 1989

Related U.S. Application Data

[63] Continuation of Ser. No. 86,287, Aug. 17, 1987, abandoned.

[30] Foreign Application Priority Data

| Aug. 26, 1986 | [JP] | Japan | 61-198136 |
| Sep. 3, 1986 | [JP] | Japan | 61-205849 |
| Sep. 18, 1986 | [JP] | Japan | 61-217916 |
| Sep. 18, 1986 | [JP] | Japan | 61-217917 |
| Nov. 18, 1986 | [JP] | Japan | 61-272825 |
| Dec. 2, 1986 | [JP] | Japan | 61-285913 |

[51] Int. Cl.$^4$ .............................. C09K 15/00
[52] U.S. Cl. .................... 252/397; 252/398
[58] Field of Search ................ 252/397, 398

[56] References Cited

U.S. PATENT DOCUMENTS

| 1,982,907 | 12/1934 | Eckey | 252/397 |
| 3,419,607 | 12/1968 | Hurst . | |
| 3,579,573 | 5/1971 | Gilde et al. . | |
| 3,591,515 | 7/1971 | Lovely | 252/187 |
| 3,792,177 | 2/1974 | Wakatani et al. | 252/397 |
| 3,875,220 | 4/1975 | White et al. . | |
| 3,911,080 | 10/1975 | Mehl et al. | 423/210 |
| 4,124,631 | 11/1978 | Hayami et al. . | |
| 4,148,822 | 4/1979 | Ogawa et al. . | |
| 4,273,676 | 6/1981 | Matsumoto et al. . | |
| 4,711,741 | 12/1987 | Fujishima et al. | 252/188.28 |
| 4,719,133 | 1/1988 | Woudsma | 252/397 |

FOREIGN PATENT DOCUMENTS

| 48-32079 | 10/1973 | Japan . |
| 57-1441 | 1/1982 | Japan . |
| 58-36619 | 3/1983 | Japan . |
| 59-39243 | 3/1984 | Japan . |
| 60-161307 | 8/1985 | Japan . |
| 1578865 | 11/1980 | United Kingdom . |

OTHER PUBLICATIONS

Chem. Abst. 30452c, vol. 72 (1970).
Chem. Abst. 96:167915w, (1982).
Chem. Abst. 99:58205f, (1983).
Chem. Abst. 101:37380d (1984).
Chem. Abst. 104:71235g (1986).

*Primary Examiner*—Paul Lieberman
*Assistant Examiner*—Willie J. Thompson
*Attorney, Agent, or Firm*—Henry C. Nields

[57] ABSTRACT

Disclosed herein is an ethylene removal agent, a postharvest preservation agent to keep freshness of vegetables, fruits and flowers, and a deodorant comprising (A) at least one compound selected from the group consisting of phosphoric acid, phosphorous acid, hypophosphorous acid, hypochlorous acid and salts of these acids, and (B) specified metal(s) or compound(s) of metal.

18 Claims, No Drawings

ETHYLENE REMOVAL AGENT, POSTHARVEST PRESERVATION AGENT AND DEODORANT

This application is a continuation of application Ser. No. 086,287 filed Aug. 17, 1987, abandoned.

BACKGROUND OF THE INVENTION

The present invention relates to an ethylene removal agent having an excellent activity of adsorbing and decomposing ethylene present in air or other atmospheres and a postharvest preservation agent which can be utilized to maintain the freshness of postharvest vegetables, fruits and flowers by mainly removing ethylene evolved from them.

Besides, the present invention relates to a deodorant which adsorbs and decomposes foul-smelling substances and is broadly utilized for deodorizing garbages, refrigerators, toilets, hospitals, hotels, ranches, sewage disposing plants, etc.

(A) As plants are still alive after being harvested, various physiological effects such as respiration effect, transpiration effect, mold growth and putrefaction under the action of microorganisms, etc. may take place together and accelerate the loss of freshness of the plants. In addition, plants evolve ethylene, a kind of plant hormone, as a metabolite. Ethylene has many physiological effects, among which there are respiratory promoting effect and maturity promoting effect, and, therefore, largely relates to maturity and also loss of freshness of the plants. The loss of freshness has been a problem especially in the storage or the distribution of vegetables, fruits and flowers. As the postharvest preservation to maintain freshness of vegetables, fruits and flowers, the following two methods are currently employed.

(1) A method of depressing the above physiological effects by controlling the storage conditions to low temperature, reduced pressure, low oxygen concentration, etc.

(2) A method of removing the evolved ethylene by an adsorbent or a catalyst.

Of the above two methods, the method (1) cannot be said to be easily accessible from the viewpoint that it requires special and complicated devices. In the method (2), the use of an adsorbent such as active carbon, zeolite, etc. to adsorb and remove ethylene has been proposed. Such adsorbents, however, have the defects that (1) the amount of adsorption is limited due to the saturated amount of adsorption, that (2) the adsorption ability is decreased with time on use and that (3) the once adsorbed ethylene is concentrated on the surface of the adsorbent and desorbed from the surface.

Accordingly, alternate methods have been proposed, wherein catalyst component or reactive species such as potassium permanganate, potassium bromate, etc. are carried on the adsorbent to convert adsorbed ethylene to other species. However, the thus treated adsorbents have not sufficient activity at ordinary conditions of use. It cannot be said that the defect of the adsorbent has been improved.

Other methods of utilizing oxidation activity of gaseous chlorine dioxide have been proposed. For instance, in Japanese Patent Publication No. 48-32079 (1973), a method has been disclosed wherein an aqueous solution of a chlorite is adsorbed on a basic adsorbent and stabilized, and the thus treated adsorbent is mixed with an acidic powder to generate gaseous chlorine dioxide.

Furthermore, in Japanese Patent Application Laid-Open (KOKAI) No. 59-39243 (1984), a composition which is able to generate gaseous chlorine dioxide has been disclosed, wherein it is prepared by impregnating a porous inorganic carrier with an aqueous solution of a chlorite adjusted to pH 9 to 14.

However, the method of using gaseous chlorine dioxide may not be practical, because it is difficult to control the amount of generation of the gas and also to prevent its decomposition during the storage of itself. Moreover, the activity no more exists when all chlorite on the carrier is decomposed. Besides, there are some cases where the generation of chlorine dioxide is undesirable in consideration of the environmental pollution.

In addition to these, even if ethylene can be removed by the use of above ethylene removal agents, sufficient postharvest preservation will not be expected. It is difficult for them to inhibit the growth of mold and putrefaction In the present invention, it is intended to provide a novel ethylene removal agent and a postharvest preservation agent which have not the above defects in the conventional methods.

(B) There are many varieties of sources of the generation of offensive odors, such as garbages in daily life, refrigerators, factories, ranches, sewage disposing plants, etc. Besides, there are many places having odor not offensive but characteristic, such as hospitals, hotels, restaurants, etc.

As the substances which cause these offensive odors, ammonia, mercaptans, sulfides, amines, aldehydes, etc. have attracted the attention. However, the actual situation is more complicated and the causes of offensive odors are not limited to the above substancs.

In recent years, many researches for removing the offensive odors have been performed with the raise of the demand for the methods of removing these offensive odors. Typical methods now available are summarized as follows.

(1) The masking method by using aromatic substances of pleasant smell to mask that of foul-smelling substances.

(2) The adsorption method of adsorbing the foul-smelling substances by using adsorbents such as active carbon.

(3) The acid-base neutralization method of neutralizing the foul-smelling substances with acids or bases.

(4) The chemical oxidation or reduction method of chemically decomposing the foul-smelling substances.

However, each method listed above has serious defects. The masking method cannot be said to be a substantial method. The adsorption method has a limit of the amount of adsorption due to the saturated amount of adsorption and is not effective against strong offensive odors. The acid-base neutralization method is limited to the substances which can be neutralized and, therefore the odors which can be removed are limited.

The chemical oxidation-reduction method is considered to be the most expected technique, though any method having a sufficient activity has not yet been found. Of the chemical oxidation-reduction methods, several techniques of utilizing the oxidation activity of gaseous chlorine dioxide have been proposed. For instance, in Japanese Patent Publication No. 48-32079 (1973), a method has been disclosed, wherein an aqueous solution of a chlorite is adsorbed to a basic adsorbent and stabilized, and the thus treated adsorbent is mixed with an acidic powder to generate gaseous chlorine dioxide. Furthermore, in Japanese Patent Application Laid-Open (KOKAI) No. 60-161307 (1985), a composition which is able to generate gaseous chlorine dioxide has been disclosed, wherein it is prepared by impregnating a porous inorganic carrier with an aqueous solution of a chlorite. However, the method of using gaseous chlorine dioxide is not practical, because it is difficult to control the amount of generation of the gas and also to prevent its decomposition during the storage of itself. Moreover, the activity no more exists when all chlorite on the carrier is decomposed. Besides, there are some cases where the generation of chlorine dioxide is undesirable in consideration of the environmental pollution.

Although each of the above methods has a deodorizing effect to some extent and is actually applied, the technical improvement of the methods has been strongly demanded from the view point of the above defects.

(C) In consideration of these background, the present inventors have investigated a highly active and stable ethylene removal agent which adsorbs and decomposes ethylene and a postharvest preservation agent which maintain freshness of vegetables, fruits and flowers and have also investigated a highly active deodorant which adsorbs and decomposes various kinds of bad odors of garbages, refrigerators, toilets, ranches, refuse disposing plants, sewage disposing plants, etc.

As a result of the investigation, the present inventors have found that a composition prepared by adding a specified compound to at least one compound selected from the group consisting of phosphoric acid, phosphorous acid, hypophosphorous acid, hypochlorous acid and the salts of these acids has a high activity of decomposing ethylene and foul-smelling substances and the composition can be used as a stable and active ethylene removal agent, a postharvest preservation agent and a deodorant which have not been hitherto known, and on the basis of these findings, the present inventors have accomplished the present invention.

SUMMARY OF THE INVENTION

In an aspect of the present invention, there is provided a ethylene removal agent, a postharvest preservation agent or a deodorant comprising (A) at least one compound selected from the group consisting of phosphoric acid, phosphorous acid hypophosphorous acid, hypochlorous acid and salts of these acids and (B) at least one compound selected from the group consisting of oxides, carbonates, sulfates, peroxides and metals of iron, cobalt, nickel, titanium, zirconium, vanadium, chromium, molybdenum, tungsten, manganese, copper, silver, zinc, germanium, tin, lead, platinum, palladium, magnesium, calcium, strontium and barium, peroxides of alkali metals, and alkali metal salts or alkaline earth metal salts of peroxocarbonic acid or peroxoboric acid.

DETAILED DESCRIPTION OF THE INVENTION

The present invention relates to an ethylene removal agent a postharvest preservation agent and a deodorant comprising (A) at least one compound selected from the group consisting of phosphoric acid, phosphorous acid, hypophosphorous acid, hypochlorous acid and salts of these acids and (B) at least one compound selected from the group consisting of oxides,carbonates, sulfates, peroxides and metals of iron, cobalt, nickel, titanium, zirconium, vanadium, chromium, molybdenum, tungsten, manganese, copper, silver, zinc, germanium, tin, lead, platinum, palladium, magnesium, calcium, strontium and barium, peroxides of alkali metals, and alkali metal salts or alkaline earth metal salts of peroxocarbonic acid or peroxoboric acid.

The characteristics of the ethylene removal agent, the postharvest preservation agent and the deodorant according to the present invention are in (1) the evolution of no gas like chlorine dioxide during the use thereof, (2) the high activity in adsorbing and decomposing ethylene and foul-smelling substances and (3) the stable activity during the use or the storage for a long period. These are the characteristics which the present inventors aimed to achieve. However, it has been found that the materials of the present invention have additional unexpected characteristics, as follows.

(1) It decomposes gases other than ethylene such as ethyl alcohol and acetaldehyde evolved from vegetables, fruits and flowers. These gases are also considered to effect on the postharvest preservation.

(2) It inhibits the growth of mold and putrefaction.

(3) It decomposes ethylene and foul-smelling substances more effectively under the circumstances of high humidity. Storage conditions of vegetables, fruits and flowers and foul-smelling places are usually humid.

Phosphoric acid, phosphorous acid, hypophosphorous acid, hypochlorous acid and salts thereof used in the invention (hereinafter referred to as "the component (A)") include the acids having different degree of hydration ( ortho acid, metha acid, polyacid, etc.), the acidic salts and the normal salts of the acids.

As the salts of phosphoric acid, phosphorous acids, hypophosphorous acid and hypochlorous acid, sodium salt, potassium salt, magnesium salt, calcium salt, barium salt, strontium salt, iron salt, cobalt salt, nickel salt, copper salt, zinc salt, zirconium salt, manganese salt, lead salt, etc. may be included.

The preferred components (A) are hypophosphorous acid, hypochlorous acid and salts thereof. Sodium salt, potassium salt, magnesium salt, calcium salt and iron salt are preferable as the salts.

While components (B) include oxides, carbonates, sulfates, peroxides and metals of iron, cobalt, nickel, titanium, zirconium, vanadium, chromium, molybdenum, tungsten, manganese, copper, silver, zinc, germanium, tin, lead, platinum, palladium, magnesium, calcium, strontium and barium, metals and oxides are preferable for platinum and palladium and oxides, carbonates, sulfates and peroxides are preferable for the other elements.

Of the components (B), those more preferable are oxides or peroxides of iron, titanium, zirconium, copper, zinc, germanium, tin, magnesim, calcium and barium, peroxides of alkali metals and alkali metal salts or alkaline earth metal salts of peroxocarbonic acid and peroxoboric acid. Of these compounds, oxides and peroxides of iron, titanium, zirconium, zinc, germanium, magnesium and calcium, peroxides of alkali metals and alkali metal salts of peroxocarbonic acid are particularly preferable.

In the case where at least one of phosphoric acid, phosphorous acid, hypophosphorous acid and the salts thereof is contained as one of the components, it is preferred that at least one of peroxides (including peroxocarbonates and peroxoborates) is added as one of the other components.

Although the component (A) and the component (B) can be used in any ratio, it is preferable to use in the ratio of component (A): component (B)=1:0.001–99 (by weight). The preferable ratio for use is component (A) : component (B)=1:0.001–30 (by weight), and particularly preferable ratio for use is component (A) : component (B)=1:0.001–10 (by weight).

The ethylene removal agent, the postharvest preservation agent and the deodorant according to the present invention can contain other active components than the components (A) and (B). As such components, for instance, chloric acid, chlorous acid and salts thereof may be employed. As the salts of chloric acid and chlorous acid, sodium salt, potassium salt, magnesium salt calcium salt, barium salt, strontium salt, etc. may be included. These active components may be employed in the preferable ratio of 0 to 50% by weight to the amount of the component (A), and more preferably in the ratio of 0 to 30% by weight.

The ethylene removal agent, the postharvest preservation agent and the deodorant of the present invention can be carried on a porous carrier. Any carrier may be used; however, the preferred carriers are silica, alumina, silica-alumina, natural zeolite, synthetic zeolite, diatomaceous earth, active carbon, clays, Kanuma earth and the like. The carrier can comprise about 10 to 90% by weight of the total composition including the carrier itself, and more preferably 30 to 90% by weight of the total composition.

The raw materials and the method of preparation of the ethylene removal agent, the postharvest preservation agent and the deodorant of the present invention are not particularly limited. As phosphoric acid, phosphorous acid, hypophosphorous acid, hypochlorous acid and the salts thereof, those ordinarily available may be used. As oxides, carbonates, sulfates, peroxides and metals of iron, cobalt, nickel, titanium, zirconium, vanadium, molybdenum, tungsten, manganese, copper, silver, zinc, germanium, tin, lead, platinum, palladium, magnesium, calcium, strontium and barium; peroxides of alkali metals and alkali metal salts and alkaline earth metal salts of peroxocarbonic acid and peroxoboric acid, reagents available can be used as they are. Alternately, oxides may be made by calcining nitrates, hydroxides or the like.

The ethylene removal agent, the postharvest preservation agent and the deodorant may be prepared by, for instance, merely mixing mechanically all the components. Or after preparing the mixture of the components (B) and the carrier, if necessary, by suitable reaction or mechanical mixing, at least one of the components (A) may be mixed mechanically or impregnated from the solution.

The thus obtained ethylene removal agent and postharvest preservation agent may be used by any suitable method. For instance, each of these agents is molded into a form of pellets and is used in a bag or a vessel having suitable gas permeability. Further, it is possible to mix these agents with film-forming materials such as polyethylene to form into films, or to apply these agents into packaging materials like papers.

The deodorant of the present invention may also be used by any suitable method. For instance, after molding the deodorant into a form of granules or pellets, it is packed into a bag or a vessel having suitable gas permeability. The thus packed deodorant can be used in refrigerators, toilets, etc. It may be possible to pass foul-smelling gasses through the layer of the deodorant of the present invention, thereby removing the odors. It may be possible to add the deodorant of the present invention directly into the source of bad odors such as sewage, garbages and the like. Moreover, it may also be possible to apply the deodorant onto or to mix the deodorant with house-building materials such as packaging materials, wallpapers and the like.

The ethylene removal agent and the postharvest preservation agent of the present invention have characteristics of decomposing low concentration of gaseous ethylene and also of keeping freshness of vegetables, fruits and flowers. This function of postharvest preservation may be due not only to its high activity of decomposing ethylene, but it has additional abilities to decompose other gases evolved and to inhibit the growth of mold and putrefaction.

Although the mechanism of decomposing ethylene by the ethylene removal agent of the present invention has not been elucidated, it is considered that it may be due mainly to catalysis. Ethylene is decomposed into carbon dioxide and the like. Therefore, different from the adsorbents and the chlorine dioxide generating agents, the ethylene removal agent and the postharvest preservation agent of the present invention can be used for a longer time period. Besides, since they have higher activity, there is a merit that a small amount thereof is enough for use. The conditions for their use are not limited. The agents sufficiently exhibit their ability even in the atmosphere controlled at low temperature of e.g. 0° C., under high humidity or under low concentration of oxygen.

The deodorant of the present invention adsorbs and converts foul-smelling substances such as ammonia, mercaptans, sulfides, amines, aldehydes and the like into odorless substances. Although its mechanism has not yet been elucidated, it is considered that it may be due mainly to catalysis. Accordingly, different from the adsorbents and the chlorine dioxide generating agents, the deodorant of the present invention can be used for a longer period. Furthermore, since it has higher activity, it has a merit that effectiveness thereof is exhibited within a short period of time. And it can be applied to the treatment of the odors of extremely high concentrations. Accordingly, the deodorant of the present invention can be utilized broadly as a deodorant.

As described above, the ethylene removal agent of the present invention is able to decompose and remove ethylene effectively present in air or other atmosphere in low concentration and is possible to be used for a long period of time without losing its activity. Therefore, it is useful as the postharvest preservation agent.

The ethylene removal agents obtained in Examples can be naturally used, as they are, as the postharvest preservation agents.

The present invention will be explained more precisely while referring to the following non-limitative examples.

EXAMPLE 1

In the presence of a small amount of water, 25 g of hypophosphorous acid, 25 g of ferric oxide and 50 g of granular silica-alumina (containing 25% by weight of alumina) were kneaded to mix uniformly, and after drying the thus obtained mixture at 110° C., the solid material obtained was pulverized into a powder of 16 to 24 meshes.

1 g of the material prepared above was placed into a vessel of a capacity of 130 ml and 20 μl of gaseous ethylene were introduced into the vessel (corresponding to about 150 ppm of ethylene). Thereafter, the change of the concentration of ethylene in the vessel at room temperature was measured by an FID gas-chromatograph. The results are shown in Table 1.

EXAMPLES 2 to 11

In the same manner as in Example 1, the materials having the compositions shown in Table 1 were obtained. The change of the concentration of ethylene with time was measured as in Example 1. The results are also shown in Table 1.

EXAMPLES 12 to 22

In the same manner as in Example 1, the materials having the compositions shown in Table 2 were obtained. The change of the concentration of ethylene with time was measured for each material as in Example 1. The results are shown in Table 2.

TABLE 1

| Example | Composition | Concentration of ethylene (ppm) after | | | | |
|---|---|---|---|---|---|---|
| | | 10 min | 20 min | 30 min | 60 min | 90 min |
| 1 | $H_3PO_2/Fe_2O_3$/silica-alumina | 55 | 25 | 11 | 0 | 0 |
| 2 | $H_3PO_2/CoO$/silica-alumina | 65 | 29 | 14 | 0 | 0 |
| 3 | $H_3PO_2$/silica-alumina | 68 | 32 | 18 | 3 | 0 |
| 4 | $H_3PO_2/TiO_2$/active carbon | 57 | 22 | 12 | 0 | 0 |
| 5 | $H_3PO_2/ZrO_2$/active carbon | 70 | 35 | 17 | 3 | 0 |
| 6 | $H_3PO_2/MnO_2$/active carbon | 63 | 20 | 15 | 0 | 0 |
| 7 | $H_3PO_2/CuO$/silica-alumina | 78 | 33 | 21 | 5 | 0 |
| 8 | $H_3PO_2/AgO$/silica-alumina | 72 | 35 | 21 | 5 | 0 |
| 9 | $H_3PO_2/SnO_2$/silica-alumina | 67 | 28 | 15 | 2 | 0 |
| 10 | $H_3PO_2/PbO$/silica-alumina | 69 | 25 | 15 | 2 | 0 |
| 11 | $H_3PO_2/Cr_2O_3$/KANUMA earth | 56 | 22 | 12 | 0 | 0 |

TABLE 2

| Example | Composition | Concentration of ethylene (ppm) after | | | | |
|---|---|---|---|---|---|---|
| | | 10 min | 20 min | 30 min | 60 min | 90 min |
| 12 | $H_3PO_2/ZnO$/silica-alumina | 50 | 21 | 8 | 0 | 0 |
| 13 | $H_3PO_2/GeO_2$/silica-alumina | 55 | 23 | 9 | 0 | 0 |
| 14 | $H_3PO_2/MgO$/silica-alumina | 59 | 25 | 10 | 0 | 0 |
| 15 | $H_3PO_2/CaCO_3$/silica-alumina | 58 | 29 | 8 | 0 | 0 |
| 16 | $H_3PO_2/SrO$/active carbon | 62 | 28 | 13 | 0 | 0 |
| 17 | $H_3PO_2/BaCO_3$/active carbon | 58 | 24 | 12 | 0 | 0 |
| 18 | $H_3PO_2/V_2O_5$/alumina | 75 | 32 | 17 | 5 | 0 |
| 19 | $H_3PO_2/MoO_3$/active carbon | 72 | 35 | 22 | 8 | 0 |
| 20 | $H_3PO_2/WO_3$/silica | 67 | 32 | 20 | 5 | 0 |
| 21 | $H_3PO_2/FeSO_4$/active carbon | 59 | 21 | 10 | 0 | 0 |
| 22 | $H_3PO_2/MgSO_4$/active carbon | 56 | 22 | 12 | 0 | 0 |

EXAMPLE 23

In the presence of a small amount of water, 20 g of hypophosphorous acid, 10 g of ferric oxide, 10 g of zinc oxide, 20 g of calcium oxide and 40 g of granular silica-alumina (containing 28% by weight of alumina) were kneaded to mix uniformly, and after drying the mixture at 110° C., the material obtained was pulverized into a powder of 16 to 24 meshes.

The change of the concentration of ethylene with time was measured for the material prepared above in the same manner as in Example 1 and the results are shown in Table 3.

EXAMPLES 24 and 25

In the same manner as in Example 23 except that phosphorous acid (Example 24) and phosphoric acid (Example 25) were used respectively instead of hypophosphorous acid, the materials having the compositions shown in Table 3 were obtained.

The change of the concentration of ethylene with time was measured for each material as in Example 1. The results are also shown in Table 3. As will be seen in Table 3, almost same results were obtained by using phosphorous acid or phosphoric acid instead of hypophosphorous acid.

EXAMPLES 26 to 28

In the same manner as in Example 23, the materials having the compositions shown in Table 3 were obtained, and the change of the concentration of ethylene with time was measured for each material in the same manner as in Example 1. The results are also shown in Table 3.

EXAMPLE 29

100 g of alumina powder were suspended in 200 ml of water, where aqueous solution of 0.265 g of chloroplatinic acid in 100 ml of water was added. The solid material obtained by evaporating the above solution to dryness was calcined for 3 hours at 450° C. in air and then was subjected to reduction with hydrogen for 2 hours at 300° C., thereby obtaining alumina supported with 0.1% by weight of platinum. The thus obtained platinum supported alumina was impregnated and carried with 25% by weight of hypophosphorous acid.

The change of the concentration of ethylene with time was measured for the material prepared above in the same manner as in Example 1. The results are shown in Table 4.

EXAMPLE 30

Example 29 was repeated except that palladium chloride and active carbon were used instead of chloroplatinic acid and alumina, respectively. The results are shown also in Table 4.

EXAMPLE 31

In the same manner as in Example 1 to 22 except that phosphoric acid phosphorous acid, sodium phosphate, sodium phosphite, or sodium hypophosphite was used instead of hypophosphorous acid in Examples 1 to 22, the corresponding materials were obtained. The change of the concentration of ethylene with time was measured for each material. Almost same results were obtained as those of Examples 1 to 22.

TABLE 3

| Example | Composition | Concentration of ethylene (ppm) after | | | | |
|---|---|---|---|---|---|---|
| | | 10 min | 20 min | 30 min | 60 min | 90 min |
| 23 | $H_3PO_2/Fe_2O_3/ZnO/CaO$/silica-alumina | 31 | 10 | 0 | 0 | 0 |
| 24 | $H_3PO_3/Fe_2O_3/ZnO/CaO$/silica-alumina | 45 | 14 | 5 | 0 | 0 |
| 25 | $H_3PO_4/Fe_2O_3/ZnO/CaO$/silica-alumina | 40 | 11 | 2 | 0 | 0 |
| 26 | $Na_3PO_2/Fe_2O_3/ZnO/CaO$/silica-alumina | 50 | 16 | 7 | 0 | 0 |
| 27 | $FePO_4/Fe_2O_3/ZnO/CaO$/silica-alumina | 46 | 12 | 3 | 0 | 0 |
| 28 | $MgHPO_4/Fe_2O_3/ZnO/CaO$/silica-alumina | 42 | 12 | 4 | 0 | 0 |

TABLE 4

| Example | Composition | Concentration of ethylene (ppm) after | | | | |
|---|---|---|---|---|---|---|
| | | 10 min | 20 min | 30 min | 60 min | 90 min |
| 29 | $H_3PO_2$/Pt/alumina | 27 | 7 | 0 | 0 | 0 |
| 30 | $H_3PO_2$/Pd/active carbon | 31 | 10 | 0 | 0 | 0 |

EXAMPLE 32:

Example 23 was repeated except that the amount of gaseous ethylene was increased to 0.26 ml (the initial concentration of ethylene in a vessel was about 2000 ppm). It was found that ethylene could not be detected after 90 minutes.

EXAMPLE 33

In the presence of a small amount of water, 25 g of calcium hypochlorite, 25 g of ferrous oxide and 50 g of granular silica-alumina (containing 28% by weight of alumina) were kneaded to mix uniformly, and after drying the mixture at 110° C, the thus obtained solid material was pulverized into powder of 16 to 24 meshes.

1 g of the material prepared above was placed into a vessel of a capacity of 230 ml, and 0.46 ml of gaseous ethylene was introduced into the vessel (corresponding to about 2000 ppm of ethylene). Then, the change of the concentration of ethylene with time was measured by an FID gaschromatograph. The results are shown in Table 5.

EXAMPLES 34 to 52

In the same manner as in Example 33, the materials having the composition shown in Table 5 were obtained. The change of the concentration of ethylene with time was measured for each material prepared above in the same manner as in Example 33. The results are shown also in Table 5.

TABLE 5

| Example | Composition | Concentration of ethylene (ppm) after | | | | |
|---|---|---|---|---|---|---|
| | | 0.5 hours | 1 hour | 2 hours | 5 hours | 24 hours |
| 33 | $Ca(ClO)_2$/FeO/silica-alumina | 21 | 3 | 0 | 0 | 0 |
| 34 | $Ca(ClO)_2$/CoO/silica-alumina | 18 | 5 | 0 | 0 | 0 |
| 35 | $Ca(ClO)_2$/NiO/silica-alumina | 25 | 8 | 0 | 0 | 0 |
| 36 | $Ca(ClO)_2/TiO_2$/silica-alumina | 35 | 10 | 3 | 0 | 0 |
| 37 | $Ca(ClO)_2/ZrO_2$/active carbon | 38 | 12 | 5 | 0 | 0 |
| 38 | $NaClO/MnO_2$/active carbon | 28 | 7 | 0 | 0 | 0 |
| 39 | NaClO/CuO/active carbon | 50 | 15 | 2 | 0 | 0 |
| 40 | $Ca(ClO)_2$/AgO/active carbon | 45 | 20 | 3 | 0 | 0 |
| 41 | $Ca(ClO)_2/SnO_2$/silica-alumina | 55 | 22 | 3 | 0 | 0 |
| 42 | $Ca(ClO)_2$/PbO/silica-alumina | 37 | 12 | 0 | 0 | 0 |
| 43 | $Ba(ClO)_2/Cr_2O_3$/NaY zeolite | 25 | 5 | 0 | 0 | 0 |
| 44 | $KClO/V_2O_5$/active carbon | 40 | 15 | 5 | 0 | 0 |
| 45 | $KClO/MoO_5$/active carbon | 37 | 18 | 3 | 0 | 0 |
| 46 | $KClO/WO_3$/active carbon | 45 | 20 | 5 | 0 | 0 |
| 47 | $Ca(ClO)_2/GeO_2$/active carbon | 35 | 12 | 0 | 0 | 0 |
| 48 | $Ca(ClO)_2/FeSO_4$/silica-alumina | 22 | 5 | 0 | 0 | 0 |
| 49 | $Ca(ClO)_2/CoSO_4$/silica-alumina | 18 | 3 | 0 | 0 | 0 |
| 50 | $Ca(ClO)_2/MgSO_4$/silica-alumina | 35 | 5 | 0 | 0 | 0 |
| 51 | $Ca(ClO)_2/CaCO_3$/silica-alumina | 58 | 8 | 1 | 0 | 0 |
| 52 | $Ca(ClO)_2/BaCO_3$/silica-alumina | 30 | 5 | 0 | 0 | 0 |

EXAMPLE 53

In the presence of a small amount of water, 20 g of calcium hypochlorite, 20 g of ferrous oxide, 10 g of zinc oxide and 50 g of granular silica-alumina (containing 28% by weight of alumina) were kneaded to mix uniformly, and after drying the mixture at 110° C., the thus obtained solid material was pulverized into powder of 16 to 24 meshes.

The ethylene removal activity of the material prepared above was measured in the same manner as in Example 33 and the results are shown in Table 6.

EXAMPLES 54 to 61

In the same manner as in Example 53, the materials having the composition shown in Table 6 were obtained. The change of the concentration of ethylene with time was measured for each material in the same manner as in Example 33. The results are also shown in Table 6.

TABLE 6

| Example | Composition | Concentration of ethylene (ppm) after | | | | |
|---|---|---|---|---|---|---|
| | | 0.5 hours | 1 hour | 2 hours | 5 hours | 24 hours |
| 53 | $Ca(ClO)_2$/FeO/ZnO/silica-alumina | 15 | 2 | 0 | 0 | 0 |
| 54 | $Ca(ClO)_2$/FeO/$GeO_2$/silica-alumina | 13 | 2 | 0 | 0 | 0 |
| 55 | $Ca(ClO)_2$/NiO/$V_2O_5$/silica-alumina | 17 | 5 | 0 | 0 | 0 |
| 56 | $Ca(ClO)_2$/NiO/$WO_3$/silica-alumina | 17 | 6 | 0 | 0 | 0 |
| 57 | $Ca(ClO)_2$/CoO/$MoO_3$/alumina | 10 | 2 | 0 | 0 | 0 |
| 58 | $Ca(ClO)_2$/FeO/$MgCO_3$/silica-alumina | 13 | 1 | 0 | 0 | 0 |
| 59 | $Ca(ClO)_2$/$TiO_2$/$Fe_2O_3$/active carbon | 10 | 1 | 0 | 0 | 0 |
| 60 | $Ca(ClO)_2$/FeO/$BaCO_3$/active carbon | 15 | 3 | 0 | 0 | 0 |
| 61 | $Ca(ClO)_2$/FeO/SrO/active carbon | 17 | 4 | 0 | 0 | 0 |

EXAMPLE 62

100 g of alumina powder were suspended into 200 ml of water, where an aqueous solution of 0.265 g of chloroplatinic acid in 100 ml of water was added. The solid material obtained by evaporating the above solution to dryness was calcined for 3 hours at 450° C. in air and then was subjected to reduction with hydrogen for 2 hours at 300° C., thereby obtaining alumina supported with 0.1% by weight of platinum. The thus obtained platinum supported alumina was impregnated and carried with 25% by weight of calcium hypochlorite.

In the same manner as in Example 33, the change of the concentration of ethylene with time was measured for the material prepared above. The results are shown in Table 7.

EXAMPLE 63

Example 62 was repeated except that palladium chloride and active carbon were used instead of chloroplatinic acid and alumina, respectively. The results are also shown in Table 7.

EXAMPLE 64

In the presence of a small amount of water, 25 g of calcium hypochlorite, 25 g of barium oxide and 50 g of granular silica-alumina (containing 28% by weight of alumina) were kneaded to mix uniformly, and after drying the mixture at 110° C., the thus obtained solid material was pulverized into powder of 16 to 24 meshes.

1 g of the material prepared above was placed into a vessel of a capacity of 230 ml and 0.46 ml of gaseous ethylene was introduced into the vessel (the concentration of ethylene in the vessel was about 2000 ppm). The change of the concentration of ethylene with time at room temperature was measured. The results are shown in Table 8.

EXAMPLES 65 to 68

In the same manner as in Example 64 except that magnesium oxide (Example 65), calcium oxide (Example 66), strontium oxide (Example 67) and zinc oxide (Example 68) were used instead of barium oxide in Example 64, the materials shown in Table 8 were obtained, respectively.

The change of the concentration of ethylene with time was measured for each material. The results are shown in Table 8.

EXAMPLE 69

136.4 g of barium nitrate and 146.2 g of zinc nitrate were dissolved into 800 ml of water, where 200 g of granular silica-alumina were added. After evaporating the above solution to dryness under agitation, the solid material obtained was pulverized into a powder of 16 to 24 meshes and calcined for 4 hours at 500 C. The composition of the powder obtained was BaO:ZnO:silica-alumina=20:10:50 (by weight).

200 ml of 10% calcium hypochlorite aqueous solution were added to 80 g of the thus obtained powder, which was evaporated to dryness under agitation and dried at 110° C.

The change of the concentration of ethylene with time was measured in the same manner as in Example 64. As a result, the concentration of ethylene, which was initially about 2000 ppm, was changed to almost zero after 2 hours and remained zero even after 24 hours.

Thereafter, 0.46 ml of ethylene was repeatedly introduced into the vessel every 24 hours, and the change of the concentration of ethylene with time was measured. The results are shown in Table 9. As is seen in the table, the activity was maintained for a long period of time.

TABLE 7

| Example | Composition | Concentration of ethylene (ppm) after | | | | |
|---|---|---|---|---|---|---|
| | | 0.5 hour | 1 hour | 2 hours | 5 hours | 24 hours |
| 62 | $Ca(ClO)_2$/Pt/alumina | 8 | 1 | 0 | 0 | 0 |
| 63 | $Ca(ClO)_2$/Pd/active carbon | 10 | 2 | 0 | 0 | 0 |

TABLE 8

| Example | Composition | Concentration of ethylene (ppm) after | | | | |
|---|---|---|---|---|---|---|
| | | 1 hour | 3 hours | 5 hours | 8 hours | 24 hours |
| 64 | $Ca(ClO)_2$/BaO/silica-alumina | 25 | 8 | 0 | 0 | 0 |
| 65 | $Ca(ClO)_2$/MgO/silica-alumina | 32 | 5 | 0 | 0 | 0 |
| 66 | $Ca(ClO)_2$/CaO/silica-alumina | 20 | 3 | 0 | 0 | 0 |
| 67 | $Ca(ClO)_2$/SrO/silica-alumina | 36 | 9.5 | 0.2 | 0 | 0 |
| 68 | $Ca(ClO)_2$/ZnO/silica-alumina | 20 | 4.1 | 0 | 0 | 0 |

TABLE 9

| Operation | Concentration of ethylene (ppm) after | | | | |
|---|---|---|---|---|---|
| | 1 hour | 3 hours | 5 hours | 8 hours | 24 hours |
| Introducing ethylene to a concentration of 2000 ppm | 2 | 0 | 0 | 0 | 0 |
| Introducing ethylene to a concentration of 2000 ppm after 24 hours | 5 | 0.5 | 0 | 0 | 0 |
| Introducing ethylene to a concentration of 2000 ppm after 48 hours | 4 | 0.7 | 0 | 0 | 0 |

EXAMPLES 70 to 73

In the same manner as in Example 69, the materials having the compositions shown in Table 10 were prepared, respectively. The change of the concentration of ethylene with time was measured for each material. The results are shown in Table 10.

TABLE 10

| Example | Composition | Concentration of ethylene (ppm) after | | | | |
|---|---|---|---|---|---|---|
| | | 1 hour | 3 hours | 5 hours | 8 hours | 24 hours |
| 70 | KClO/MgO/BaCO$_3$/active carbon | 5 | 0.5 | 0 | 0 | 0 |
| 71 | Ba(ClO)$_2$/CaO/ZnO/NaY zeolite | 3 | 0.2 | 0 | 0 | 0 |
| 72 | Ca(ClO)$_2$/SrO/ZnO/diatomaceous earth | 3 | 0.1 | 0 | 0 | 0 |
| 73 | Ca(ClO)$_2$/MgCO$_3$/silica-alumina | 45 | 10 | 0 | 0 | 0 |

EXAMPLE 74

In the presence of a small amount of water, 15 g of calcium hypochlorite, 10 g of sodium chlorite, 25 g of titanium oxide and 150 g of active carbon powder were kneaded to mix uniformly, and the mixture obtained was dried at 110° C.

The change of the concentration of ethylene with time was measured for the material obtained above. The results are shown in Table 11.

TABLE 11

| Example | Composition | Concentration of ethylene (ppm) after | | | | |
|---|---|---|---|---|---|---|
| | | 30 min. | 1 hour | 2 hours | 5 hours | 24 hours |
| 74 | Ca(ClO)$_2$/NaClO$_2$/TiO$_2$/active carbon | 28 | 8 | 0 | 0 | 0 |

EXAMPLE 75

50 g of 50% hypophosphorous acid aqueous solution were added to 50 g of active carbon powder, and after mixing, 25 g of calcium peroxide were further added. After mixing uniformly, the mixture was dried at 110° C.

The change of the concentration of ethylene with time was measured for the material obtained above in the same manner as in Example 1. The results are shown in Table 12.

EXAMPLES 76 and 77

In the same manner as in Example 75 except that 50% phosphorous acid aqueous solution (Example 76) and 50% phosphoric acid aqueous solution (Example 77) were used instead of 50% hypophosphorous acid aqueous solution, two kinds of the materials shown in Table 12 were obtained, respectively. The change of the concentration of ethylene with time was measured for each material in the same manner as in Example 1. The results are shown in Table 12.

EXAMPLE 78

20 g of 50% hypophosphorous acid aqueous solution were added to 40 g of active carbon powder and mixed, followed by adding 20 g of zinc oxide and 20 g of calcium peroxide and mixing uniformly. The mixture was dried at 110° C.

The change of the concentration of ethylene with time was measured for the material obtained above in the same manner in Example 1. The results are also shown in Table 12.

EXAMPLES 79 to 87

In the same manner as in Example 78, the materials having the compositions shown in Table 12 were obtained and the change of the concentration of ethylene with time was measured for each material. The results are also shown in Table 12.

EXAMPLE 88

Each of 1 kg of green tangerine, 1 kg of peach and 1 kg of brocoli was sealed in a polyethylene bag of 0.03 mm thickness together with 2 g of the material prepared in Example 53, respectively and stored at room temperature in order to evaluate the ability as the postharvest preservation agent. The results are shown in Table 13 together with the results of the control without the agent.

TABLE 12

| Example | Composition | Concentration of ethylene (ppm) after | | | | |
|---|---|---|---|---|---|---|
| | | 10 min | 20 min | 30 min | 60 min | 90 min |
| 75 | H$_3$PO$_2$/CaO$_2$/active carbon | 32 | 14 | 4 | 0 | 0 |
| 76 | H$_3$PO$_3$/CaO$_2$/active carbon | 40 | 16 | 8 | 0 | 0 |
| 77 | H$_3$PO$_4$/CaO$_2$/active carbon | 36 | 13 | 5 | 0 | 0 |
| 78 | H$_3$PO$_2$/CaO$_2$/ZnO/active carbon | 20 | 7 | 0 | 0 | 0 |
| 79 | H$_3$PO$_2$/CaO$_2$/TiO$_2$/zeolite | 17 | 6 | 0 | 0 | 0 |

TABLE 12-continued

| Example | Composition | Concentration of ethylene (ppm) after | | | | |
|---|---|---|---|---|---|---|
| | | 10 min | 20 min | 30 min | 60 min | 90 min |
| 80 | MgHPO$_4$/CaO$_2$/GeO$_2$/zeolite | 28 | 12 | 0 | 0 | 0 |
| 81 | H$_3$PO$_4$/K$_2$O$_2$/Fe$_2$O$_3$/zeolite | 25 | 9 | 0 | 0 | 0 |
| 82 | H$_3$PO$_2$/Na$_2$O$_2$/active carbon | 38 | 18 | 8 | 0 | 0 |
| 83 | H$_3$PO$_2$/K$_2$O$_2$/active carbon | 40 | 19 | 9 | 0 | 0 |
| 84 | FePO$_4$/BaO$_2$/active carbon | 39 | 15 | 5 | 0 | 0 |
| 85 | H$_3$PO$_2$/sodium peroxocarbonate/active carbon | 43 | 17 | 8 | 0 | 0 |
| 86 | H$_3$PO$_2$/sodium peroxoborate/active carbon | 45 | 20 | 12 | 0 | 0 |
| 87 | H$_3$PO$_2$/magnesium peroxoborate/active carbon | 49 | 22 | 14 | 2 | 0 |

TABLE 13

| Days of storage | Green tangerine | | Peach | | Brocoli | |
|---|---|---|---|---|---|---|
| | Control | Used | Control | Used | Control | Used |
| 1 | no change | no change | no change | no change | no change | no change |
| 2 | no change | no change | no change | no change | slightly yellowed | no change |
| 3 | no change | no change | partly changed in colour | no change | yellowed | no change |
| 4 | slightly yellowed | no change | brown spots | no change | completely yellowed | no change |
| 5 | slightly yellowed | no change | began to rot | no change | began to mold | no change |
| 6 | yellowed | no change | completely rotten | no change | rotten | slightly yellowed |
| 7 | yellowed | no change | — | dark red | — | — |
| 8 | partly rotten | no change | — | dark red | — | — |
| 30 | partly rotten | half yellowed | — | — | — | — |

EXAMPLES 89 to 92

Three kiwi fruits were sealed in each polyethylene bag of 0.03 mm thickness together with 1 g of each of the materials prepared in Examples 53, 59, 74 and 79 and stored at room temperature. The results were compared with those of the control in which the above materials were not used. The fruits of the control were completely softened after 30 days, while the fruits stored in each bag with each material maintained the initial hardness even after 30 days.

EXAMPLES 93 to 95

Two apples were sealed in a polyethylene bag of 0.03 mm thickness together with 1 g of each of the materials prepared in Examples 23, 59 and 79 and stored at room temperature. The results were compared with those of the control in which the above materials were not used. As the results, the upper part of the apples of the control were changed into brown in colour and began to get out the shape after 30 days, while the apples stored with the above materials remained unchanged in the shape and the taste.

EXAMPLES 96 and 97

In a polyethylene bag of 0.03 mm thickness were sealed 200 g of white mushroom together with 1 g of each of the materials prepared in Examples 53 and 79 and stored at room temperature, which were compared with the control.

As the results, the white mushrooms of the control changed into brown in colour on the 2nd day, while those stored with the above materials remained unchanged in colour even after 4 days. In addition, ethyl alcohol was detected in the former, but not in the latter, which suggests that ethyl alcohol was decomposed by the materials used.

EXAMPLE 98

A block of broccoli was sealed in a polyethylene bag together with 1 g of the material prepared in Example 23 and stored at room temperature, which was compared with the control.

As the results, the brocoli of the control changed completely into yellow on the 4th day and began to rot on the 6th day, while the brocoli stored with the material kept the initial green colour after 6 days.

EXAMPLE 99 to 101

1 kg of cherries was packed in a corrugated carton with 5 g of the material prepared in Examples 53, 59 and 78, respectively and stored at room temperature.

As the results, all of them kept unchanged after 7 days, while cherries of the control were partly turned black and the mold was observed on a part of cherries after 3 days.

EXAMPLE A-1

In the presence of a small amount of water, 25 g of hypophosphorous acid, 25 g of ferric oxide and 50 g of granular silica-alumina (containing 28% by weight of alumina) were kneaded to mix uniformly, and after drying the thus obtained mixture at 110 C, the solid material obtained was pulverized into powder of 16 to 24 meshes to obtain a deodorant.

After sealing 1 g of the thus obtained deodorant in a polyethylene vessel together with 500 ml of a sample gas containing 1000 ppm of methylmercaptan, 500 ppm of hydrogen sulfide and 500 ppm of ammonia, the concentration of each component of the gas in the vessel was measured by gaschromatography. The results are shown in Table A-1.

EXAMPLES A-2 to A-11

In the same manner as in Example A-1, the deodorants having the compositions shown in Table A-1 were obtained, respectively. The activity of each of the deodorants was measured in the same manner as in Example A-1 and the results are shown in Table A-1.

EXAMPLES A-12 to A-22

In the same manner as in Example A-1, the deodorants having the compositions shown in Table A-2 were obtained, respectively. The activity of each of the deodorants was measured in the same manner as in Example A-1 and the results are shown in Table A-2.

EXAMPLE A-23

In the presence of a small amount of water, 20 g of hypophosphorous acid, 20 g of zinc oxide, 20 g of calcium peroxide and 40 g of active carbon powder were kneaded to mix uniformly, and after drying the mixture obtained at 110° C., the solid material obtained was pulverized to powder of 16 to 24 meshes to obtain a deodorant.

The activity of the deodorant was measured in the same manner as in Example A-1 and the results are shown in Table A-3.

EXAMPLES A-24 and A-25

In the same manner as in Example A-23 except that phosphorous acid (Example A-24) and phosphoric acid (Example A-25) are used instead of hypophosphorous acid, the deodorants having the compositions shown in Table A-3 were obtained, respectively. The activity of each of the deodorants was measured in the same manner as in Example A-1 and the results are shown in Table A-3.

As is clearly seen in the table, almost the same results were obtained by using phosphorous acid or phosphoric acid instead of hypophosphorous acid.

EXAMPLES A-26 to A-31

In the same manner as in Example A-23, the deodorants having the compositions shown in Table A-3 were obtained, respectively and the activity of each of the deodorants was measured in the same manner as in Example A-1. The results are also shown in Table A-3.

TABLE A-1

| Example | Composition | Substance | Concentration (ppm) after | | |
|---|---|---|---|---|---|
| | | | 30 min | 1 hour | 2 hours |
| A-1 | $H_3PO_2/Fe_2O_3$/Silica-alumina | methylmercaptan | 20 | 0 | 0 |
| | | hydrogen sulfide | 15 | 0 | 0 |
| | | ammonia | 32 | 5 | 0 |
| A-2 | $H_3PO_2/CoO$/Silica-alumina | methylmercaptan | 25 | 0 | 0 |
| | | hydrogen sulfide | 11 | 0 | 0 |
| | | ammonia | 25 | 2 | 0 |
| A-3 | $H_3PO_2NiO$/Silica-alumina | methylmercaptan | 31 | 2 | 0 |
| | | hydrogen sulfide | 15 | 0 | 0 |
| | | ammonia | 27 | 3 | 0 |
| A-4 | $H_3PO_2/TiO_2$/active carbon | methylmercaptan | 29 | 0 | 0 |
| | | hydrogen sulfide | 22 | 1 | 0 |
| | | ammonia | 34 | 5 | 0 |
| A-5 | $H_3PO_2/ZrO_2$/active carbon | methylmercaptan | 25 | 0 | 0 |
| | | hydrogen sulfide | 17 | 0 | 0 |
| | | ammonia | 21 | 2 | 0 |
| A-6 | $H_3PO_2MnO_2$/active carbon | methylmercaptan | 32 | 3 | 0 |
| | | hydrogen sulfide | 20 | 0 | 0 |
| | | ammonia | 25 | 3 | 0 |
| A-7 | $H_3PO_2/CuO$/active carbon | methylmercaptan | 37 | 5 | 0 |
| | | hydrogen sulfide | 20 | 0 | 0 |
| | | ammonia | 30 | 5 | 0 |
| A-8 | $H_3PO_2/AgO$/Silica-alumina | methylmercaptan | 37 | 3 | 0 |
| | | hydrogen sulfide | 15 | 0 | 0 |
| | | ammonia | 26 | 3 | 0 |
| A-9 | $H_3PO_2SnO_2$/Silica-alumina | methylmercaptan | 42 | 5 | 0 |
| | | hydrogen sulfide | 20 | 0 | 0 |
| | | ammonia | 25 | 2 | 0 |
| A-10 | $H_3PO_2PbO$/Silica-alumina | methylmercaptan | 32 | 2 | 0 |
| | | hydrogen sulfide | 20 | 0 | 0 |
| | | ammonia | 28 | 3 | 0 |
| A-11 | $H_3PO_2/Cr_2O_3$/KANUMA EARTH | methylmercaptan | 28 | 5 | 0 |
| | | hydrogen sulfide | 21 | 0 | 0 |
| | | ammonia | 23 | 0 | 0 |

TABLE A-2

| Example | Composition | Substance | Concentration (ppm) after | | |
|---|---|---|---|---|---|
| | | | 30 min | 1 hour | 2 hours |
| A-12 | $H_3PO_2/ZnO$/Silica-alumina | methylmercaptan | 22 | 0 | 0 |
| | | hydrogen sulfide | 15 | 0 | 0 |
| | | ammonia | 18 | 0 | 0 |
| A-13 | $H_3PO_2/GeO_2$/Silica-alumina | methylmercaptan | 27 | 2 | 0 |
| | | hydrogen sulfide | 16 | 0 | 0 |
| | | ammonia | 20 | 5 | 0 |
| | $H_3PO_2/MgO$/Silica- | methylmercaptan | 26 | 2 | 0 |

TABLE A-2-continued

| Example | Composition | Substance | Concentration (ppm) after 30 min | 1 hour | 2 hours |
|---|---|---|---|---|---|
| A-14 | alumina | hydrogen sulfide | 15 | 0 | 0 |
| | | ammonia | 21 | 5 | 0 |
| A-15 | $H_3PO_2$/$CaCO_3$/Silica-alumina | methylmercaptan | 38 | 7 | 0 |
| | | hydrogen sulfide | 22 | 0 | 0 |
| | | ammonia | 28 | 5 | 0 |
| A-16 | $H_3PO_2$/SrO/active carbon | methylmercaptan | 32 | 5 | 0 |
| | | hydrogen sulfide | 18 | 0 | 0 |
| | | ammonia | 23 | 5 | 0 |
| A-17 | $H_3PO_2$/$BaCO_3$/active carbon | methylmercaptan | 35 | 5 | 0 |
| | | hydrogen sulfide | 18 | 0 | 0 |
| | | ammonia | 25 | 5 | 0 |
| A-18 | $H_3PO_2$/$V_2O_5$/alumina | methylmercaptan | 45 | 10 | 0 |
| | | hydrogen sulfide | 28 | 5 | 0 |
| | | ammonia | 35 | 10 | 0 |
| A-19 | $H_3PO_2$/$MoO_3$/active carbon | methylmercaptan | 35 | 5 | 0 |
| | | hydrogen sulfide | 20 | 0 | 0 |
| | | ammonia | 30 | 8 | 0 |
| A-20 | $H_3PO_2$/$WO_3$/Silica | methylmercaptan | 42 | 5 | 0 |
| | | hydrogen sulfide | 25 | 0 | 0 |
| | | ammonia | 35 | 8 | 0 |
| A-21 | $H_3PO_2$/$FeSO_4$/active carbon | methylmercaptan | 35 | 3 | 0 |
| | | hydrogen sulfide | 15 | 0 | 0 |
| | | ammonia | 25 | 7 | 0 |
| A-22 | $H_3PO_2$/$MgSO_4$/active carbon | methylmercaptan | 27 | 0 | 0 |
| | | hydrogen sulfide | 18 | 0 | 0 |
| | | ammonia | 25 | 5 | 0 |

TABLE A-3

| Example | Composition | Substance | Concentration (ppm) after 15 min. | 30 min. | 60 min. |
|---|---|---|---|---|---|
| A-23 | $H_3PO_2$/ZnO/$CaO_2$/active carbon | methylmercaptan | 10 | 0 | 0 |
| | | hydrogen sulfide | 5 | 0 | 0 |
| | | ammonia | 25 | 5 | 0 |
| A-24 | $H_3PO_3$/ZnO/$CaO_2$/active carbon | methylmercaptan | 12 | 0 | 0 |
| | | hydrogen sulfide | 6 | 0 | 0 |
| | | ammonia | 27 | 8 | 0 |
| A-25 | $H_3PO_4$/ZnO/$CaO_2$/active carbon | methylmercaptan | 12 | 0 | 0 |
| | | hydrogen sulfide | 5 | 0 | 0 |
| | | ammonia | 25 | 8 | 0 |
| A-26 | $Na_3PO_2$/ZnO/$CaO_2$/active carbon | methylmercaptan | 25 | 5 | 0 |
| | | hydrogen sulfide | 12 | 0 | 0 |
| | | ammonia | 30 | 10 | 0 |
| A-27 | $FePO_4$/ZnO/$CaO_2$/active carbon | methylmercaptan | 28 | 8 | 0 |
| | | hydrogen sulfide | 15 | 0 | 0 |
| | | ammonia | 32 | 11 | 0 |
| A-28 | $MgHPO_4$/ZnO/$CaO_2$/active carbon | methylmercaptan | 25 | 3 | 0 |
| | | hydrogen sulfide | 15 | 0 | 0 |
| | | ammonia | 28 | 9 | 0 |
| A-29 | $H_3PO_2$/$CaO_2$/$TiO_2$/active carbon | methylmercaptan | 27 | 2 | 0 |
| | | hydrogen sulfide | 16 | 0 | 0 |
| | | ammonia | 20 | 5 | 0 |
| A-30 | $MgHPO_4$/$CaO_2$/$GeO_2$/zeolite | methylmercaptan | 26 | 2 | 0 |
| | | hydrogen sulfide | 15 | 0 | 0 |
| | | ammonia | 21 | 5 | 0 |
| A-31 | $H_3PO_4$/$K_2O_2$/$Fe_2O_3$/zeolite | methylmercaptan | 28 | 7 | 0 |
| | | hydrogen sulfide | 22 | 0 | 0 |
| | | ammonia | 28 | 5 | 0 |

EXAMPLE A-32

50% hypophosphorous acid aqueous solution were added to 50 g of active carbon powder and mixed, where 25 g of calcium peroxide were added. After mixing uniformly, the mixture was dried at 110° C. to obtain a deodorant. The activity of the deodorant was measured in the same manner as in Example A-1. The results are shown in Table A-4.

EXAMPLES A-33 and A-34

In the same manner as in Example A-32 except that 50% phosphorous acid aqueous solution (Example A-33) and 50% phosphoric acid aqueous solution (Example A-34) were used instead of 50% hypophosphorous acid aqueous solution, the deodorants having the compositions shown in Table A-4 were obtained, respectively.

The activity of each of the deodorants was measured in the same manner as in Example A-1 and the results are shown in Table A-4.

EXAMPLES A-35 to A-40

In the same manner as in Example A-32, the deodorants having the compositions shown in Table A-4 were obtained, respectively and the activity of each of the deodorants was measured in the same manner as in Example A-1. The results are shown in Table A-4.

TABLE A-4

| Example | Composition | Substance | Concentration (ppm) after | | |
|---|---|---|---|---|---|
| | | | 15 min | 30 min | 60 min |
| A-32 | $H_3PO_2/CaO_2$/active carbon | methylmercaptan | 25 | 7 | 0 |
| | | hydrogen sulfide | 10 | 3 | 0 |
| | | ammonia | 30 | 10 | 0 |
| A-33 | $H_3PO_3/CaO_2$/active carbon | methylmercaptan | 30 | 10 | 0 |
| | | hydrogen sulfide | 15 | 5 | 0 |
| | | ammonia | 35 | 12 | 0 |
| A-34 | $H_3PO_4/CaO_2$/active carbon | methylmercaptan | 28 | 7 | 0 |
| | | hydrogen sulfide | 15 | 5 | 0 |
| | | ammonia | 32 | 10 | 0 |
| A-35 | $H_3PO_2/Na_2O_2$/active carbon | methylmercaptan | 29 | 9 | 0 |
| | | hydrogen sulfide | 15 | 5 | 0 |
| | | ammonia | 32 | 11 | 0 |
| A-36 | $H_3PO_2/K_2O_2$/active carbon | methylmercaptan | 27 | 9 | 0 |
| | | hydrogen sulfide | 12 | 5 | 0 |
| | | ammonia | 33 | 12 | 0 |
| A-37 | $FePO_4/BaO_2$/silica-alumina | methylmercaptan | 45 | 15 | 0 |
| | | hydrogen sulfide | 25 | 8 | 0 |
| | | ammonia | 40 | 13 | 0 |
| A-38 | $H_3PO_2$/sodium peroxoborate/active carbon | methylmercaptan | 27 | 9 | 0 |
| | | hydrogen sulfide | 13 | 6 | 0 |
| | | ammonia | 33 | 11 | 0 |
| A-39 | $H_3PO_2$/sodium peroxoborate/active carbon | methylmercaptan | 28 | 10 | 0 |
| | | hydrogen sulfide | 18 | 8 | 0 |
| | | ammonia | 37 | 15 | 0 |
| A-40 | $H_3PO_2$/magnesium peroxoborate/active carbon | methylmercaptan | 31 | 12 | 0 |
| | | hydrogen sulfide | 18 | 9 | 0 |
| | | ammonia | 45 | 15 | 0 |

EXAMPLE A-41

100 g of alumina powder were suspended in 200 ml of water, where an aqueous solution of 0.265 g of chloroplatinic acid in 100 ml of water was added. The solid material obtained by evaporating the mixture to dryness was calcined for 3 hours at 450° C. in air, and then was subjected to reduction with hydrogen for 2 hours at 300° C., thereby obtaining alumina supported with 0.1% by weight of platinum. The thus obtained platinum supported alumina was impregnated and carried with 25% by weight of hypophosphorous acid to obtain a deodorant. The activity of the deodorant was measured in the same manner as in Example A-1 and the results are shown in Table A-5.

EXAMPLE A-42

Example A-41 was repeated except that palladium chloride and active carbon were used instead of chloroplatinic acid, and alumina, respectively. The results are also shown in Table A-5.

EXAMPLE A-43

In the same manner as in Example A-1 to A-22 except that phosphoric acid sodium phosphate, sodium phosphate, sodium phosphite or sodium hypophopsphite was used instead of hypophosphorous acid in Example A-1 to A-22, the deodorants were obtained and the activity of each of the deodorants was measured in the same manner as in Example A-1. Almost same results were obtained as those of Example A-1 to A-22.

TABLE A-5

| Example | Composition | Substance | Concentration (ppm) after | | |
|---|---|---|---|---|---|
| | | | 15 min. | 30 min. | 60 min. |
| A-41 | $H_3PO_2$/Pt/alumina | methylmercaptan | 15 | 0 | 0 |
| | | hydrogen sulfide | 9 | 0 | 0 |
| | | ammonia | 20 | 0 | 0 |
| A-42 | $H_3PO_2$/Pd/active carbon | methylmercaptan | 12 | 0 | 0 |
| | | hydrogen sulfide | 10 | 0 | 0 |
| | | ammonia | 22 | 0 | 0 |

EXAMPLE A-44

10 g of the deodorant prepared in Example A-23 were packed in a paper bag and three bags prepared above were placed in three different places in a public toilet of an area of 15 m². As a result, the so-called odor of the toilet was removed and the effect of the deodorant did not change after 3 months.

EXAMPLE A-45

After packing 10 g of the deodorant prepared in Example A-23 in a paper bag, it was fixed on the inside of the cover of a polyethylene bucket of a capacity of 30 l containing raw garbage. As the result, the bad odor of the raw garbage was removed and the effect did not change after one month.

EXAMPLE A-46

In the presence of a small amount of water, 25 g of calcium hypochlorite, 25 g of ferrous oxide and 50 g of granular silica-alumina (containing 28% by weight of alumina) were kneaded to mix uniformly, and after drying the mixture at 110° C., the obtained solid material was pulverized into powder of 16 to 24 mesh to obtain a deodorant.

After sealing 1 g of the thus obtained deodorant in a polyethylene vessel together with 500 ml of a sample gas containing 1000 ppm of methylmercaptan, 500 ppm of hydrogen sulfide and 1000 ppm of ammonia, the change of the concentration of each of the components in the vessel was measured. The results are shown in Table A-6.

EXAMPLES A-47 to A-56

In the same manner as in Example A-46, the deodorants having the compositions shown in Table A-6 were obtained, respectively. The activity of the deodorants was measured and the results are also shown in Table A-6.

EXAMPLE A-66

In the presence of a small amount of water, 20 g of calcium hypochlorite, 20 g of ferrous oxide, 10 g of zinc oxide and 50 g of granular silica-alumina (containing 28% by weight of alumina) were kneaded to mix uniformly, and after drying the mixture at 110° C., the obtained solid material was pulverized into powder of 16 to 24 meshes to obtain a deodorant.

The activity of the deodorant was measured in the same manner as in Example A-46 and the results are shown in Table A-8.

EXAMPLES A-67 to A-72

In the same manner as in Example A-66, the deodorants having the compositions shown in Table A-8 were obtained, respectively. The activity of each of the deodorants was measured and the results are also shown in Table A-8.

TABLE A-6

| Example | Composition | Substance | Concentration (ppm) after | | |
|---|---|---|---|---|---|
| | | | 30 min | 1 hour | 2 hours |
| A-46 | $Ca(ClO)_2$/FeO/Silica-alumina | methylmercaptan | 20 | 2 | 0 |
| | | hydrogen sulfide | 15 | 0 | 0 |
| | | ammonia | 15 | 0 | 0 |
| A-47 | $Ca(ClO)_2$/CoO/Silica-alumina | methylmercaptan | 15 | 0 | 0 |
| | | hydrogen sulfide | 11 | 0 | 0 |
| | | ammonia | 10 | 0 | 0 |
| A-48 | $Ca(ClO)_2$/NiO/Silica-alumina | methylmercaptan | 25 | 1 | 0 |
| | | hydrogen sulfide | 18 | 0 | 0 |
| | | ammonia | 19 | 2 | 0 |
| A-49 | $Ca(ClO)_2$/$TiO_2$/mordenite | methylmercaptan | 22 | 0 | 0 |
| | | hydrogen sulfide | 16 | 0 | 0 |
| | | ammonia | 20 | 0 | 0 |
| A-50 | $Ca(ClO)_2$/$ZrO_2$/active carbon | methylmercaptan | 25 | 0 | 0 |
| | | hydrogen sulfide | 10 | 0 | 0 |
| | | ammonia | 10 | 0 | 0 |
| A-51 | $Ca(ClO)_2$/AgO/active carbon | methylmercaptan | 23 | 0 | 0 |
| | | hydrogen sulfide | 18 | 0 | 0 |
| | | ammonia | 15 | 0 | 0 |
| A-52 | $Ca(ClO)_2$/$SuO_2$/Silica-alumina | methylmercaptan | 30 | 0 | 0 |
| | | hydrogen sulfide | 12 | 0 | 0 |
| | | ammonia | 15 | 0 | 0 |
| A-53 | $Ca(ClO)_2$/PbO/Silica-alumina | methylmercaptan | 25 | 0 | 0 |
| | | hydrogen sulfide | 17 | 0 | 0 |
| | | ammonia | 18 | 0 | 0 |
| A-54 | $Ca(ClO)_2$/$GeO_2$/active carbon | methylmercaptan | 30 | 2 | 0 |
| | | hydrogen sulfide | 15 | 0 | 0 |
| | | ammonia | 20 | 2 | 0 |
| A-55 | $Ca(ClO)_2$/$CaCO_3$/Silica-alumina | methylmercaptan | 32 | 1 | 0 |
| | | hydrogen sulfide | 18 | 1 | 0 |
| | | ammonia | 18 | 0 | 0 |
| A-56 | $Ca(ClO)_2$/$BaCO_3$/Silica-alumina | methylmercaptan | 35 | 0 | 0 |
| | | hydrogen sulfide | 15 | 0 | 0 |
| | | ammonia | 12 | 0 | 0 |

EXAMPLES A-57 to A-65

In the same manner as in Example A-46, the deodorants having the compositions shown in Table A-7 were obtained, respectively. The activity of each of the deodorants was measured in the same manner as in Example A-46 and the results are shown in Table A-7.

TABLE A-7

| Example | Composition | Substance | Concentration (ppm) after | | |
|---|---|---|---|---|---|
| | | | 30 min | 1 hour | 2 hours |
| A-57 | $NaClO$/$MnO_2$/active carbon | methylmercaptan | 28 | 0 | 0 |
| | | hydrogen sulfide | 19 | 0 | 0 |
| | | ammonia | 23 | 0 | 0 |
| A-58 | $NaClO$/CuO/active carbon | methylmercaptan | 30 | 2 | 0 |
| | | hydrogen sulfide | 15 | 0 | 0 |
| | | ammonia | 20 | 1 | 0 |
| A-59 | $KClO$/$V_2O_5$/active carbon | methylmercaptan | 20 | 0 | 0 |
| | | hydrogen sulfide | 12 | 0 | 0 |
| | | ammonia | 15 | 0 | 0 |
| A-60 | $KClO$/$MoO_3$/active carbon | methylmercaptan | 29 | 2 | 0 |
| | | hydrogen sulfide | 15 | 0 | 0 |
| | | ammonia | 21 | 1 | 0 |
| A-61 | $KClO$/$WO_3$/active carbon | methylmercaptan | 35 | 5 | 0 |
| | | hydrogen sulfide | 22 | 2 | 0 |
| | | ammonia | 25 | 0 | 0 |
| A-62 | $Ba(ClO)_2$/$Cr_2O_3$/NaY | methylmercaptan | 22 | 0 | 0 |
| | | hydrogen sulfide | 13 | 0 | 0 |

TABLE A-7-continued

| Example | Composition | Substance | Concentration (ppm) after 30 min | 1 hour | 2 hours |
|---|---|---|---|---|---|
| | zeolite | ammonia | 12 | 0 | 0 |
| | | methylmercaptan | 25 | 0 | 0 |
| A-63 | $Ca(ClO)_2/FeSO_4$/Silica-alumina | hydrogen sulfide | 12 | 0 | 0 |
| | | ammonia | 16 | 0 | 0 |
| | | methylmercaptan | 21 | 0 | 0 |
| A-64 | $Ca(ClO)_2/CoSO_4$/Silica-alumina | hydrogen sulfide | 12 | 0 | 0 |
| | | ammonia | 14 | 0 | 0 |
| | | methylmercaptan | 27 | 0 | 0 |
| A-65 | $Ca(ClO)_2/MgSO_4$/Silica-alumina | hydrogen sulfide | 18 | 0 | 0 |
| | | ammonia | 22 | 0 | 0 |

TABLE A-8

| Example | Composition | Substance | Concentration (ppm) after 30 min | 1 hour | 2 hours |
|---|---|---|---|---|---|
| | | methylmercaptan | 16 | 0 | 0 |
| A-66 | $Ca(ClO)_2/FeO/ZnO$/Silica-alumina | hydrogen sulfide | 10 | 0 | 0 |
| | | ammonia | 12 | 0 | 0 |
| | | methylmercaptan | 15 | 0 | 0 |
| A-67 | $Ca(ClO)_2/FeO/GeO_2$/Silica-alumina | hydrogen sulfide | 11 | 0 | 0 |
| | | ammonia | 10 | 0 | 0 |
| | | methylmercaptan | 20 | 0 | 0 |
| A-68 | $Ca(ClO)_2/CoO/MoO_3$/alumina | hydrogen sulfide | 8 | 0 | 0 |
| | | ammonia | 10 | 0 | 0 |
| | | methylmercaptan | 18 | 0 | 0 |
| A-69 | $Ca(ClO)_2/FeO/MgCO_3$/Silica | hydrogen sulfide | 15 | 0 | 0 |
| | | ammonia | 15 | 0 | 0 |
| | | methylmercaptan | 15 | 0 | 0 |
| A-70 | $Ca(ClO)_2/FeO/CaO$/active carbon | hydrogen sulfide | 7 | 0 | 0 |
| | | ammonia | 10 | 0 | 0 |
| | | methylmercaptan | 17 | 0 | 0 |
| A-71 | $Ca(ClO)_2/FeO/BaCO_3$/active carbon | hydrogen sulfide | 9 | 0 | 0 |
| | | ammonia | 12 | 0 | 0 |
| | | methylmercaptan | 18 | 0 | 0 |
| A-72 | $Ca(ClO)_2/FeO/SrO$/active carbon | hydrogen sulfide | 12 | 0 | 0 |
| | | ammonia | 10 | 0 | 0 |

EXAMPLE A-73

100 g of alumina powder were suspended in 200 ml of water, where an aqueous solution of 0.265 g of chloroplatinic acid in 100 ml of water was added. The mixture obtained was evaporated to dryness under agitation and the obtained solid material was calcined for 3 hours at 450° C. in air and then was reduced by hydrogen for 2 hours at 300° C. to obtain alumina supported with 0.1% by weight of platinum. The thus obtained platinum supported alumina was impregnated and carried with 25% by weight of calcium hypochlorite to obtain a deodorant. The activity of the deodorant was examined in the same manner as in Example A-46. The results are shown in Table A-9.

EXAMPLE A-74

Example A-73 was repeated except that palladium chloride and active carbon were used instead of chloroplatinic acid and alumina, respectively. The results are also shown in Table A-9.

EXAMPLE A-75

In the presence of a small amount of water, 25 g of calcium hypochlorite, 25 g of zinc oxide and 50 g of granular silica-alumina (containing 28% by weight of alumina) were kneaded to mix uniformly and after drying the mixture at 110° C., the obtained solid material was pulverized into powder of 16 to 24 meshes to obtain a deodorant.

After sealing 1 g of the deodorant in a polyethylene vessel together with 500 ml of a sample gas containing 1000 ppm of methylmercaptan, 500 ppm of hydrogen sulfide and 1000 ppm of ammonia, the change of the concentration of each of the components was measured. The results are shown in Table A-10.

EXAMPLES A-76 to A-79

Example A-75 was repeated except that magnesium oxide (Example A-76), calcium oxide (Example A-77), barium oxide (Example A-78) and strontium oxide (Example A-79) were used respectively instead of zinc oxide to obtain the deodorants shown in Table A-10.

TABLE A-9

| Example | Composition | Substance | Concentration (ppm) after 30 min | 1 hour | 2 hours |
|---|---|---|---|---|---|
| A-73 | $Ca(ClO)_2/Pt$/alumina | methylmercaptan | 13 | 0 | 0 |
| | | hydrogen sulfide | 5 | 0 | 0 |
| | | ammonia | 7 | 0 | 0 |
| A-74 | $Ca(ClO)_2/Pd$/active carbon | methylmercaptan | 11 | 0 | 0 |
| | | hydrogen sulfide | 5 | 0 | 0 |
| | | ammonia | 5 | 0 | 0 |

The activity of each of the deodorants was measured and the results are also shown in Table A-10.

EXAMPLE A-80

136.4 g of barium nitrate and 146.2 g of zinc nitrate were dissolved into 800 ml of water, where 200 g of silica-alumina were added. After evaporating the mixture to dryness under agitation, the obtained solid material was pulverized into powder to 16 to 24 meshes and then calcined for 4 hours at 500° C. The composition of the solid material obtained was BaO:ZnO:silica-alumina= 20:10:50 (by weight).

200 ml of 10% calcium hypochlorite aqueous solution were added to 80 g of the solid material obtained above and the mixture was evaporated to dryness and dried at 110° C. to obtain a deodorant.

After sealing 1 g of the deodorant in a polyethylene vessel together with 500 ml of a sample gas containing 11000 ppm of methylmercaptan, the change of the concentration of methylmercaptan was measured The results are shown in Table A-11.

COMPARATIVE EXAMPLE

A test was carried out in the same manner as in Example A-80 while using the composition shown in Table A-11 and the test results are shown in Table A-11.

EXAMPLE A-81 to A-84

In the same manner as in Example A-80, the deodorants having the compositions shown in Table A-12 were prepared, and the activity of each of the deodorants was measured in the same manner as in Example A-75 The results are shown in Table A-12.

TABLE A-11

| | | Concentration of methylmercaptan (ppm) after | | |
|---|---|---|---|---|
| | Composition | 30 min. | 1 hour | 2 hours |
| Example A-80 | $Ca(ClO)_2$BaO/ZnO/ silica-alumina | 150 | 12 | 0 |
| Comparative Example | $Ca(ClO)_2$ silica-alumina BaO/ZnO/silica-alumina | 7700 9680 8910 | 7975 9570 8800 | 7560 9500 8820 |

TABLE A-12

| | | | Concentration (ppm) after | | |
|---|---|---|---|---|---|
| Example | Composition | Substance | 30 mm | 1 hour | 2 hours |
| A-81 | $KClO/MgO/BaCO_3$/ active carbon | methylmercaptan hydrogen sulfide ammonia | 45 35 40 | 8 5 5 | 0 0 0 |
| A-82 | $Ba(ClO)_2$/CaO/ZnO/ NaY zeolite | methylmercaptan hydrogen sulfide ammonia | 60 45 52 | 10 2 7 | 0 0 0 |
| A-83 | $Ca(ClO)_2$/SrO/ZnO/ diatomaceous earth | methylmercaptan hydrogen sulfide ammonia | 35 25 30 | 5 2 3 | 0 0 0 |
| A-84 | $Ca(ClO)_2/MgCO_3$/ silica-alumina | methylmercaptan hydrogen sulfide ammonia | 70 52 55 | 12 8 10 | 0 0 0 |

EXAMPLES A-85 and A-86

100 g of dehydrated sewage sludge were placed into a glass bottle of 2 l in capacity and covered with 2 g of the deodorants prepared in Example A-23 and A-29, respectively.

After the closely sealed bottle was allowed to stand for 24 hours at 30° C., the concentrations of methylmercaptan and hydrogen sulfide were measured.

As a result, they were 200 ppm and 100 ppm, respectively, in the test without the deodorants, while the concentrations of both compounds were less than 1 ppm in each test.

What we claim is:

1. A method for removing ethylene from an ethylene-generating source, which method comprises placing in proximity to said source a composition which comprises (A) at least one compound selected from the group consisting of phosphoric acid, phosphorous acid, hypophosphorous acid, hypochlorous acid an salts of said acids and (B) at least one compound selected from the group consisting of oxides, carbonates, sulfates and peroxides of cobalt, nickel, titanium, zirconium, vanadium, chromium, molybdenum, tungsten, manganese,

TABLE A-10

| | | | Concentration (ppm) after | | |
|---|---|---|---|---|---|
| Example | Composition | Substance | 30 min | 1 hour | 2 hours |
| A-75 | $Ca(ClO)_2$/ZnO/silica-alumina | methylmercaptan hydrogen sulfide ammonia | 25 10 15 | 2 1 2 | 0 0 0 |
| A-76 | $Ca(ClO)_2$/MgO/silica-alumina | methylmercaptan hydrogen sulfide ammonia | 38 25 25 | 4 5 4 | 0 0 0 |
| A-77 | $Ca(ClO)_2$/CaO/silica-alumina | methylmercaptan hydrogen sulfide ammonia | 35 22 27 | 4 4 5 | 0 0 0 |
| A-78 | $Ca(ClO)_2$/BaO/silica-alumina | methylmercaptan hydrogen sulfide ammonia | 45 35 50 | 5 3 7 | 0 0 0 |
| A-79 | $Ca(ClO)_2$/SrO/silica-alumina | methylmercaptan hydrogen sulfide ammonia | 51 43 47 | 6 5 7 | 0 0 0 | copper, silver, zinc, germanium, tin, lead, platinum, palladium, magnesium, calcium, strontium, and barium, $Fe_2O_3$, peroxides of alkali metals, and alkali metal salts or alkaline earth metal salts of peroxocarbonic acid or peroxoboric acid.

2. A method for preserving harvested fruits, vegetables or flowers, which method comprises placing in proximity to said fruits, vegetables or flowers a composition which comprises (A) at least one compound selected from the group consisting of phosphoric acid, phosphorous acid, hypophosphorous acid, hypochlorous acid and salts of said acids and (B) at least one compound selected from the group consisting of oxides, carbonates, sulfates, and peroxides of cobalt, nickel, titanium, zircomium, vanadium, chromium, molybdenmm, tungsten, manganese, copper, silver, zinc, germanium, tin, lead, platinum, palladium, magnesium, calcium, strontium, and barium, $Fe_2O_3$, peroxides of alkali metals and alkali metal salts or alkaline earth metal salts of peroxocarbonic acid or peroxoboric acid.

3. A method for deodorizing a gas which comprises odorous substances, which method comprises bringing said gas into contact with a composition which comprises (A) at least one compound selected from the group consisting of phosphoric acid, phosphorous acid, hypophosphorous acid and hypochlorite and (B) at least one compound selected from the group consisting of oxides and peroxides of iron, nickel, titanium, zirconium, vanadium, chromium, molybdenum, tungsten, copper, silver, zinc, germanium, tin, lead, platinum, palladium, magnesium, calcium, strontium, and barium, peroxides of alkali metals, and alkali metal salts or alkaline earth metal salts of peroxocarboniacid or peroxoboric acid.

4. A method for deodorizing an odor-generating source, which method comprises adding to said source a composition which comprises (A) at least one compound selected from the group consisting of phosphoric acid, phosphorous acid, hypophosphorous acid and hypochlorite and (B) at least one compound selected from the group consisting of oxides and peroxides of iron, nickel, titanium, zirconium, vanadium, chromium, molybdenum, tungsten, copper, silver, zinc, germanium, tin, lead, platinum, palladium, magnesium, calcium, strontium, and barium, peroxides of alkali metals and alkali metal salts or alkaline earth metal salts of peroxocerbonic acid or peroxoboric acid.

5. A method according to claim 1, 2, 3 or 4, wherein the weight ratio of the component (A) to the compound (B) is in the range of 1:0.001-99.

6. A method according to claim 1, 2, 3 or 4, wherein the weight ratio of the component (A) to the component (B) is in the range of 1:0.001-30.

7. A method according to claim 1 or 2, wherein the component (A) is at least one compound selected from the group consisting of phosphoric acid, hypophosphorous acid and calcium hypochlorite.

8. A method according to claim 1 or 2, wherein the component (B) is at least one compound selected from the group consisting of oxides or peroxides of titanium, zirconium, copper, zinc, germanium, tin, magnesium, calcium and barium, $Fe_2O_3$, peroxides of alkali metals, and alkali metal salts or alkaline earth metal salts or peroxocarbonic acid or peroxoboric acid.

9. A method according to claim 1 or 2, wherein the component (B) is at least one compound selected from the group consisting of $Fe_2O_3$, zinc oxidide and calcium peroxide.

10. A method according to claim 1 or 2, wherein the component (A) is at least one compound selected from the group consisting of phosphoric acid, hypophosphorous acid, and calcium hypochlorite and the component (B) is at least one compound selected from the group consisting of oxides or peroxides of titanium, zirconium, copper, zinc, germanium, tin, magnesium, calcium and barium, $Fe_2O_3$, peroxides of alkali metals, and alkali metal salts or alkaline earth metal salts of peroxocarbonic acid or peroxoboric acid.

11. A method according to claim 10, wherein the component (B) is at least one compound selected from the group consisting of $Fe_2O_3$, zinc oxide and calcium peroxide.

12. A method according to claim 3 or 4, wherein the component (A) is phosphoric acid.

13. A method according to claim 3 or 4, wherein the component (B) is at least one compound selected from the group consisting of oxides and peroxides of iron, titanium, zirconium, copper, zinc, germanium, tin, magnesium, calcium and barium, peroxides of alkali metals, and alkali metal salts or alkaline earth metal salts of peroxocarbonic acid or peroxoboric acid.

14. A method according to claim 3 or 4, wherein the component (B) is at least one compound selected from the group consisting of $Fe_2O_3$, titanium oxide and calcium peroxide.

15. A method according to claim 3 or 4, wherein the component (A) is phosphoric acid and the component (B) is at least one compound selected from the group consisting of oxides and peroxides of iron, titanium, zirconium, copper, zinc, germanium, tin, magnesium, calcium and barium, peroxides of alkaline metals, and alkali metal salts or alkaline earth metal salts of peroxocarbonic acid or peroxoboric acid.

16. A method according to claim 15, wherein the component (B) is at least one compound selected from the group consisting of $Fe_2O_3$, titanium oxide and calcium, peroxide.

17. A method according to claim 1, 2, 3 or 4, wherein the component (A) and the component (B) have been carried on a carrier.

18. A method according to claim 17, wherein said carrier is at least one carrier selected from the group consisting of silica, alumina, silica-alumina, natural zeolite, synthetic zeolite, diatomaceous earth, Kanuma earth, clays and active carbon.

* * * * *